United States Patent
Moskvin et al.

(10) Patent No.: US 9,545,527 B2
(45) Date of Patent: Jan. 17, 2017

(54) SYSTEM DESIGN AND METHOD FOR VERIFYING 3D DOSIMETRIC IMAGING OF CHARGED PARTICLES IN MEDIA

(71) Applicants: INDIANA UNIVERSITY RESEARCH AND TECHNOLOGY CORPORATION, Indianapolis, IN (US); PURDUE RESEARCH FOUNDATION, West Lafayette, IN (US)

(72) Inventors: Vadim Moskvin, Memphis, TN (US); Keith Michael Stantz, Carmel, IN (US)

(73) Assignees: Purdue Research Foundation, West Lafayette, IN (US); St. Jude Children's Research Hospital, Inc., Memphis, TN (US)

( * ) Notice: Subject to any disclaimer, the term of this patent is extended or adjusted under 35 U.S.C. 154(b) by 0 days.

(21) Appl. No.: 14/888,363

(22) PCT Filed: Apr. 30, 2014

(86) PCT No.: PCT/US2014/036112
§ 371 (c)(1),
(2) Date: Oct. 30, 2015

(87) PCT Pub. No.: WO2014/179430
PCT Pub. Date: Nov. 6, 2014

(65) Prior Publication Data
US 2016/0074675 A1 Mar. 17, 2016

Related U.S. Application Data

(60) Provisional application No. 61/818,104, filed on May 1, 2013.

(51) Int. Cl.
*A61N 5/00* (2006.01)
*A61N 5/10* (2006.01)
(Continued)

(52) U.S. Cl.
CPC .............. *A61N 5/1071* (2013.01); *A61B 8/08* (2013.01); *A61B 8/483* (2013.01); *A61N 5/1039* (2013.01);
(Continued)

(58) Field of Classification Search
CPC .............. A61N 5/1071; A61N 5/1039; A61N 2005/1034; A61N 2005/1087; A61B 8/483; A61B 8/08; A61B 2019/524
(Continued)

(56) References Cited

U.S. PATENT DOCUMENTS 4,385,634 A * 5/1983 Bowen .................. A61B 5/416
600/407
6,309,352 B1 10/2001 Oraevsky et al.
(Continued)

OTHER PUBLICATIONS

Tada, et al ("Time resolved properties of acoustic pulses generated in water and in soft tissue by pulsed proton beam irradiation—a possibility of doses distribution monitoring in proton radiation therapy" Medical Physics 18, 1100 (1991)).*
(Continued)

*Primary Examiner* — Michael Maskell
(74) *Attorney, Agent, or Firm* — Eschweiler & Associates, LLC

(57) ABSTRACT

A method of verifying therapeutic beam delivery accuracy by ultrasound tomographic imaging to map three dimensional (3D) dose through the detection of ionizing radiation induced thermo-acoustic signal from the proton beam.

20 Claims, 16 Drawing Sheets

(51) Int. Cl.
*A61B 8/08* (2006.01)
*A61B 19/00* (2006.01)

(52) U.S. Cl.
CPC .. *A61B 2019/524* (2013.01); *A61N 2005/1034* (2013.01); *A61N 2005/1087* (2013.01)

(58) Field of Classification Search
USPC .......................................... 250/492.1, 492.3
See application file for complete search history.

(56) References Cited

U.S. PATENT DOCUMENTS

| | | |
|---|---|---|
| 6,567,688 B1 | 5/2003 | Wang |
| 2010/0171504 A1* | 7/2010 | Nichiporov .......... A61N 5/1048 324/464 |

OTHER PUBLICATIONS

Assmann, et al ("Ionoacoustic characterization of the proton Bragg peak with submillimeter accuracy" Medical Physics 42, 567 (2015)).*
Nichiporov D. Moskvin V, Fanelli L, Das U. Range shift and dose perturbation with high-density materials in proton beam therapy. Nuclear Instruments & Methods in Physics Research Section B—Beam Interactions with Materials and Atoms. 2011;269(22):2685-92. doi: 10.1016/j.nimb.2011.07.109. PubMed PMID:WOS :000296113600009.
Moskvin V. Cheng CW, Fanelli L, Zhao L, Das IT. A semi-empirical model for the therapeutic range shift estimation caused by imhomogeneities in proton beam therapy. Journal of Applied Clinical Medical Physics. 2012;13 (2):3-12. PubMed PMID: WOS :000304140300002.
Vynckier S, Derreumaux S, Richard F. Bol A, Michel C, Wambersie A. Is it Possible to Verify Directly a Proton-Treatment Plan Using Positron Emission Tomography. Radiother Oncol. 1993;26(3):275-7. doi: 10.1016/0167-8140(93)90271-9. PubMed PMID: WOS:A1993LA51600012.
Min CH, Kim CH, Youn MY, Kim JW. Prompt gamma measurements for locating the dose falloff region in the proton therapy. Applied Physics Letters. 2006;89(18). doi: 10.1063/1.2378561. PubMed PM1D: WOS:000241757500134.
MM CH, Lee HR, Kim CH, Lee SB. Development of array-type prompt gamma measurement system for in vivo range verification in proton therapy. Med Phys. 2012;39(4):2100-7. doi 10.1118/1.3694098. PubMed PMID: WOS:000302371900039.
Espana S. Zhu X, Daartz J, El Fakhri G, Bortfeld T, Paganetti H. The reliability of proton-nuclear interaction cross-section data to predict proton-induced PET images in proton therapy. Physics in Medicine and Biology. 2011:56(9):2687-98. doi:1088/0031-9155/56/9/003. PubMed PMID: WOS:000289346000003.
Knopf AC, Parodi K, Paganetti H, Bortfled T, Daartz J, Engelsman M, et al. Accuracy of Proton Beam Range Verification Using Post-treatment Positron Emission Tomography/Computed Tomography as Function of Treatment Site. International Journal of Radiation Oncology Biology Physics. 2011;79(1):297-304. doi: 10.1016/j.ijrobp.2010.02.017. PubMed PMID: WOS :000285656600042.
Knopf A, Parodi K, Bortfeld T. Shih HA, Paganetti H. Systematic analysis of biological and physical limitations of proton beam range verification with offline PET/CT scans. Physics in Medicine and Biology. 2009;54(14):4477-95. doi: 10.1088/0031-9155/54/14/008. PubMed PMID: WOS:00026770100008.
Espana S, Paganetti H. The impact of uncertainties in the CT conversion algorithm when predicting proton beam ranges in patients from dose and PET-activity distributions. Physics in Medicine and Biology. 2010;55(24):7557-71. doi: 10.1088/0031-9155/55/24/011. PubMed PMID: W05:000284825200011.
Polf JC, Peterson S, Ciangaru G, Gillin M, Beddar S. Prompt gamma-ray emission from biological tissues during proton irradiation: a preliminary study. Physics in Medicine and Biology. 2009;54(3):731-43. doi: 10.1088/0031-9155/54/3/017. PubMed PMID: WOS :000262359000017.
Askaryan GA. Hydrodynamic radiation from the tracks of ionizing particles in stable liquids. The Soviet Journal of Atomic Energy. 1957;3(2):921-3. doi: 10.1007/BF01480076.
Baily NA. A Review of the Processes by Which Ultrasound Is Generated Through the Interaction of Ionizing-Radiation and Irradiated Materials—Some Possible Applications. Med Phys. 1992;19(3):525-32. doi: 10.1118/1.596842. PubMed PMID: WOS:A1992HZ95800001.
De Bonis G. Acoustic signals from proton beam interaction in water—Comparing experimental data and Monte Carlo simulation. Nucl Instrum Methods Phys Res Sect A—Accel Spectrom Dect Assoc Equip. 2009;604(1-2):S199-S202. doi: 10.1016/j.nima.2009.03.072. PubMed PMID: ISI:000267922600045.
Graf K, Anton G, Hossl J, Kappes A, Karg T, Katz U, et al. Testing thermo-acoustic sound generation in water with proton and laser beams. Int J Mod Phys A. 2006:21:127-31. PubMed PMID: ISI: 000239988200024.
Lyamshev LM. Radiation Acoustics. Uspekhi Fiz Nauk. 1992;162(4):43-94. PubMed PMID: ISI:AI 992HW72800002.
Thompson LF. Acoustic detection of ultra-high-energy neutrinos. Nuclear Instruments and Methods in Physics Research Section A: Accelerators, Spectrometers, Detectors and Associated Equipment. 2008;588(1-2):155-61. doi: http ://dx .doi.org/10.1016/j .nima.2008.01.031.
Volovik VD, Kalinichenko AI, Lazurik VT, Popov GF. The acoustic detection of high-energy particles in water. Physics Letters A. 1979:70(5-6):495-6. doi: Doi: 10.1016/0375-9601(79)90377-3.
Albul VI, Bychkov VB, Vasil'ev SS, Gusev KE, Demidov VS, Demidova EV, et al. Acoustic field generated by a beam of protons stopping in a water medium. Acoust Phys. 2005;51(1):33-7. PubMed PMID: ISI:000227199200004.
Battistoni G, Muraro S, Sala PR, Cerutti F, Ferrari A, Roesler S, et al. The FLUKA code: Description and benchmarking. M. Albrow, R. Raja editors. Proceedings of the Hadronic Shower Simulation Workshop 2006, Fermilab Sep. 6-8, 2006, A1P Conference Proceedings. 2007;896:31-49.
Ferrari A, Sala PR, Fasso A, Ranft J. Fluka: a multi-particle transport code. CERN Oct. 2005, INFN/TC_05/11, SLAC-R-773. 2005. Attorney Vynckier S, Derreumaux S, Richard F, et al. Is it possible to verify directly a proton-treatment plan using positron emission tomography? Radiother Oncol. 1993;26:275-7.
Moteabbed M, Esparia S, Paganetti H. Monte Carlo patient study on the comparison of prompt gamma and PET imaging for range verification in proton therapy. Physics in Medicine and Biology. 2011;56:1063-1082.
Sulak L, Armstrong T, Baranger H, et al. Experimental studies of the acoustic signature of proton beams traversing fluid media. Nuclear Instruments and Methods 161 (1979) 203-217.
Kruger RA, Liu P, Fang YR, et al. Photoacoustic ultrasound (PAUS) reconstruction tomography. Med Phys. 1995:22:1605-1609.
Kruger RA, Liu P. Photoacoustic ultrasound: pulse production and detection of 0.5% Liposyn. Med Phys. 1994;21: I 1 79/1184.
Yuan Y, Xing D, Xiang L. High-contrast photoacoustic imaging based on filtered back-projection algorithm with velocity potential integration. In: vol. 7519.; 2009:75190L-75190L-8.
Knopf A-C, Lomax A. In vivo proton range verification: a review. Phys Med Biol. 2013:58:R131-160.
Smeets J, Roellinghoff F, Prieels D, et al. Prompt gamma imaging with a slit camera for real-time range control in proton therapy. Phys Med Biol. 2012;57:3371-3405.
Hayakawa Y, Tada J. Arai N, et al. Acoustic pulse generated in a patient during treatment by pulsed proton radiation beam. Radiation Oncology Investigations. 1995;3:42-45.
Matthews JN. Accelerators shrink to meet growing demand for proton therapy. Physics Today. 2009;62:22.
Peggs S, Satogata T. Flanz J. A survey of hadron therapy accelerator technologies. In: Particle Accelerator Conference. 2007, PAC. IEEE.; :115-119.

(56) References Cited

OTHER PUBLICATIONS

Caporaso GJ, Mackie TR, Sampayan S, et al. A compact linac for intensity modulated proton therapy based on a dielectric wall accelerator. Phys Med. 2008;24:98-101.

Linz U, Alonso J. What will it take for laser driven proton accelerators to be applied to tumor therapy? Physical Review Special Topics—Accelerators and Beams. 2007;10:094801.

Murakami M, Demizu Y, Niwa Y, et al. Current Status of the HIBMC, Providing Particle Beam Radiation Therapy for More Than 2,600 Patients, and the Prospects of Laser-Driven Proton Radiotherapy. IFMBE Proceedings, 2009, vol. 25 (1), pp. 878-882.

Schwoerer H, Pfotenhauer S, Jackel O, et al. Laser-plasma acceleration of quasi-monoenergetic protons from microstructured targets, 2006;439:445-448.

Askariyan GA, Dolgoshein BA, Kalinovsky AN, Mokhov NV. Acoustic Detection of High-Energy Particle Showers in Water. Nuclear Instruments & Methods. 1979;164(2):267-78. doi: 10.1016/0029-554x(79)90244-1. PubMed PMID: WOS:A1979HG85800007.

Lyamshev LM. Radiation acoustics. Boca Raton, Fla.: CRC Press; 2004.

Barrett H.H., Swindell W. Radiological imaging the theory of image formation, detection, and processing. San Diego: Academic Press; 1981.

Albul VI, Bychkov VB, Gusev KE, Demidov VS, Demidova EV, Konovalov SL, et al. Measurements of the parameters of the acoustic radiation accompanying the moderation of an intense proton beam in water. Instrum Exp Tech. 2001:44(3):327-34. PubMed PMID: ISI:000169946100004.

Tada J, Hayakawa Y, Hosono K, et al. Time resolved properties of acoustic pulses generated in water and in soft tissue by pulsed proton beam irradiation—A possibility of doses distribution monitoring in proton radiation therapy. Medical Physics. 1991;18:1100-1104.

Flanz J, Smith A. Technology for proton therapy. Cancer J. 2009;15:292-7.

* cited by examiner

SYSTEM DESIGN AND METHOD FOR VERIFYING 3D DOSIMETRIC IMAGING OF CHARGED PARTICLES IN MEDIA

CROSS-REFERENCE TO RELATED APPLICATIONS

This application claims priority to pending PCT Application Serial No. PCT/US 14/36112 entitled "SYSTEM DESIGN AND METHOD FOR VERIFYING 3D DOSIMETRIC IMAGING OF CHARGED PARTICLES IN MEDIA," filed Apr. 30, 2014 and U.S. Provisional Application No. 61/818,104 entitled "SYSTEM DESIGN AND METHOD FOR VERIFYING 3D DOCIMETRIC IMAGING OF CHARGED PARTICLES IN MEDIA," filed May 1, 2013, which are hereby incorporated by reference.

TECHNICAL FIELD

The present disclosure relates to a method of verification of the accuracy of delivery of a therapeutic proton beam by ultrasound tomographic imaging to map three dimensional (3D) proton dose through detection of ionizing radiation induced thermo-acoustic signal from proton beam.

BACKGROUND

The dose delivered to a patient from proton therapy remains uncertain, in particular the positioning of the distal edge and lateral displacement of the proton or charged particle beam, and the dose delivered. Current treatment quality assurance methods to monitor these parameters include positron emission tomography (PET) and the detection of prompt gammas (PGs). PET is based on the detection of the production of gammas from the positron annihilation after positron decay due to proton induced nuclear reactions with endogenous molecular in human tissue, specifically oxygen, nitrogen and carbon. The detection of PGs, the emitted gamma accompanying the decay of excited nuclei from proton interactions within tissue. However, some weaknesses in these methods include sensitivity, modest spatial resolution, post-treatment assessment (for PET method), and non-linearity and accuracy of the method relative to dose deposited.

Accordingly, it remains desirable to provide a clinically viable diagnostic method of 3D dosimetric imaging and treatment beam delivery in vivo during the time of treatment (beam delivery).

BRIEF DESCRIPTION OF THE DRAWINGS

Embodiments of the present disclosure will now be described by way of example in greater detail with reference to the attached figures, in which.

DETAILED DESCRIPTION OF THE INVENTION

Figure 1:
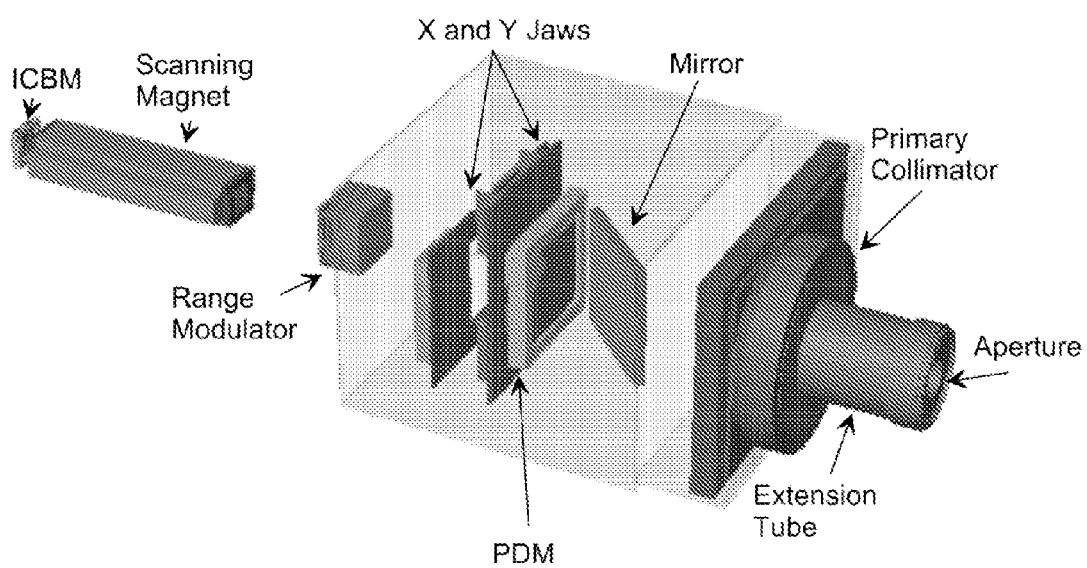
FIG. 1 is an exploded view of a treatment nozzle design for proton beam passage through a Monte Carlo (MC) simulation.

Accuracy and quantification of proton beam dose delivery via proton therapy is generally indistinct and hence invasive to patients. In addition, delivery location of the proton beam is uncertain, particularly, positioning of the distal edge and lateral displacement of the beam. The present disclosure is directed to this problem. In particular, the present disclosure relates to a method for verifying the accuracy of therapeutic proton beam delivery that increases the ability to non-invasively image the dose distribution in a patient. Further, the method presently disclosed increases the determination of the accuracy and precision of the treatment plan in order to aid potential modifications or adaptations over the time of therapy.

Charged particle therapy, especially proton therapy is a growing treatment modality. As indicated, above one challenge of the present day ion beam therapy, in particular with proton beam, is verification of the dose delivered to a patient and its exact distribution in the human body. While the initial parameters of the beam can be controlled, the exact delivery of the beam remains uncertain due to multiple factors like; tumor shrinking, orphan motion, uncertainty in the patient setup, the specificity of the treatment planning algorithm, and inhomogeneities in the humanbody. Availability to verify the position of the distal edge and lateral displacement of the beam are significant parameters of the treatment accuracy assurance.

One characteristic of the dose deposition is the 90% or 80% dose level at distal edge of the Bragg Peak or Spread Out Bragg Peak (SOBP) called proton therapeutic range. Presence of inhomogeneities in tissue like implants or bones or changes in the geometry of the area through which the beam is passing (e.g., tumor shrinking) will affect the therapeutic range and hence, may cause the deviation in the treatment.

Two current trends in developing treatment quality assurance methods to monitor the results of the delivery of charged particle therapy have emerged. Positron Emission Tomography method (PET) which is based on the detection of the gamma quanta from the positron annihilation after decay of products from proton induced nuclear reactions with oxygen, carbon in human tissue and the detection of the prompt gamma accompanied in the interaction of the protons with the tissue.

The PET method is used post-treatment and requires expensive equipment while not warranted by the results of the proton range verification in practice due to cross-sections of interaction accuracy, the patient specific tissue composition, and non-linear dependence of the positron yield on the energy particles at the place of dose delivery and dose delivered. Prompt gamma technique may be used at the time of treatment once robust detection techniques for high energy prompt photons (e.g., greater than 8 MeV) generated from tissue are developed. However, this technique does not assure the accuracy due to gamma background from other processes accompanied in the interaction of the proton beam with the tissue, including the secondary neutron interaction with the detector and luck of the robust detection methods for high energy photons and neutrons.

When direct ionizing radiation passes through the media, the energy deposition along the particle tracks leads to local overheating in the media at a nanoscale area around the particle track and fast expansion of the media.

Thermoacoustics Equation

The localized change in temperature of an object exposed to an external source is related to the rate of heat generated, $q_{ext}$, by the following equation.

$$q_{ext} = \rho c \cdot \frac{\partial T(\vec{r}, t)}{\partial t} \quad (1)$$

where $\rho$ is object mass density, c is the heat capacity of the object, and T is the temperature of the object located at r. Equation (1) relates the rate of heating $q_{ext}$ [J s$^{-1}$/cm$^3$] or dose rate [Gy/s] deposited from the proton beam to the excess temperature and heat (storage) capacity, c, of the object. This equation excludes heat conductivity which is slow and negligibly contributes to the thermacoustic pressure wave if the heating occurs over a short period of time.

The resulting excess volume expansion (dV) or acoustic displacement (u) due to the rise in temperature from the dose deposited at location r is a function of the outward force due to thermal volume expansion of the object, β, and the opposing force from the surrounding tissue due to its thermal compressibility, $\kappa_T$.

$$\nabla \cdot u = -\kappa_T p(\vec{r}, t) + \beta \cdot T(\vec{r}, t) \quad (2)$$

Inserting equation (2) into the generalized form of Hooke's law and into Newton's law (ignoring sheer forces, i.e., ∇×u=0), a generalized wave equation for thermoacoustics is derived.

$$\left(\frac{1}{v_s^2}\frac{\partial^2}{\partial t^2} - \nabla^2\right)p(\vec{r}, t) = (\Gamma v_s^{-2})\frac{\partial q_{ext}(\vec{r}, t)}{\partial t} \quad (3)$$

In the above equation, p(r,t) [Pa] is the thermally-induced pressure; $v_s$ is the velocity of sound of the medium $(\kappa_T\rho)^{-1/2}$; and Γ, the Gruneisen parameter [Pa/(J/cm$^3$) or Pa/Gy], is equal to $\beta\ c^{-1}\ (\kappa_T\rho)^{-1}$. The solution to equation (3) is obtained using time-retarded Green's function and integration over all space, d$^3$r'.

$$p(\vec{r}, t) = \frac{\Gamma \cdot v_s^{-2}}{4\pi} \cdot \iiint \frac{d^3 r'}{|\vec{r} - \vec{r}'|}\left(\frac{\partial q_{ext}(\vec{r}', t')}{\partial t'}\right)_{t'=t-\frac{|\vec{r}-\vec{r}'|}{v_s}} \quad (4)$$

For tissue this parameter is about 1.3×10$^5$ Pa/(J/cm$^3$) or 130 Pa/Gy, and approximately 20 percent lower for water (107 Pa/Gy).

Tomographic Image Reconstruction

Equation (3) can be recast into a form of a 3-dimensional (3-D) Radon transform, where the projections as defined by the velocity potential, ϕ(r,t), are related to the 2-D surface integrals defined by the retarded time, |r-r'|=$v_s$t.[9] Given that p(t)=−ρ dϕ/dt, $$\phi(r, t) = -\frac{1}{\rho} \cdot \int_0^\tau p(t')\,dt'. \quad (5)$$

Therefore, based on equations (4) and (5)

$$\phi(r, t) = -\frac{1}{\rho} \cdot \int_0^\tau p(t')\,dt' = -\frac{(\Gamma v_s^{-2})}{4\pi\rho}\iiint \frac{d^3 r'}{|r-r'|}\cdot q(\vec{r}, t'). \quad (6)$$

The dose rate from the proton beam, $q_{ext}$(r',t'), can be separated into a spatial and temporal component $\Phi_0$D(r')ℑ(t'), where $\Phi_0$ is the proton particle flux, D(r') is the deposited dose, and ℑ(t') depicts the pulse shape of the proton beam. Where a medium has a homogenous velocity of sound, the volume integral can be rewritten as a surface integral. For a rectangular pulse of protons with a width $t_{PW}$, the above equation resembles a 3-dimensional Radon transform $$\frac{1}{\rho}\int p(t')\,dt' \approx \frac{\Gamma \cdot v_s^{-2}}{4\pi}\cdot(\Phi_0 \cdot t_{PW})\cdot v_s \oiint_{|r-r'|=v_s t} D(r')\cdot \frac{dS}{v_s t} \quad (7)$$

where 1D projections $\lambda_n$ derived from the velocity potential represents the surface integral of the dose D(r') over a thin 2-D spherical shell of radius R=|r-r'|=$v_s$t centered at the position of a transducer; and n is the normal vector of the projection.

$$\lambda_{\hat{n}} = \frac{4\pi}{\rho} \frac{1}{(\Gamma \cdot v_s^2)} \frac{t}{(\Phi_0 \cdot t_{PW})} \int p(t')dt' = \oiint_{|r-r'|=v_s \cdot t} D(r') \cdot dS \quad (8)$$

The reconstructed object is calculated summing over all projection angles and taking the Laplacian, $$b(r) = \frac{1}{4\pi^2} \cdot \nabla^2 \cdot \int_{2\pi} d\Omega_n \cdot \lambda_{\hat{n}} = \frac{1}{4\pi^2} \int_{2\pi} d\Omega_n \cdot \frac{1}{v_s^2} \frac{\partial^2 \lambda_n}{\partial t^2} \bigg|_{|r-r'|=v_s t} \quad (9)$$

which is equivalent to taking the second derivative of the $\lambda_n$ of equation (8). Therefore, a 3-D filtered backprojection algorithm can be used to reconstruct the dose from the 1-D projections $$\hat{\lambda} \approx g \cdot \Gamma^{-1} \cdot t \cdot IFT\{\hat{P}(\omega) \cdot H(\omega)\}. \quad (10)$$

Each projection depends on constants relating the thermoacoustic-induced pressure to absorbed dose. The factor g represents the total number of protons per pulse ($\Phi_0 t_{PW}$) and a weighting factor $w_r$, for each projection, which depends on the geometry of the scanner. $\Gamma$ represents the effectiveness at which dose is converted to pressure based on the physical properties of the object, and t is the propagation time it takes for the pressure wave to reach the transducer from within the object. $P(\omega)$ is the measured pressure signal for a transducer, and $H(\omega)$ is the filter function, $$H(\omega) = |\omega| \cdot \frac{A(\omega)}{I(\omega)},$$

where $A(\omega)$ is an apodizing function and $I(\omega)$ is the impulse response of the transducer.

The above described effect is called radiation acoustics effect; and the resulting stress wave is detectable as an ultra-sound signal and is directly correlated with the energy deposited.

Scanner Design/Geometry

Figure 7:
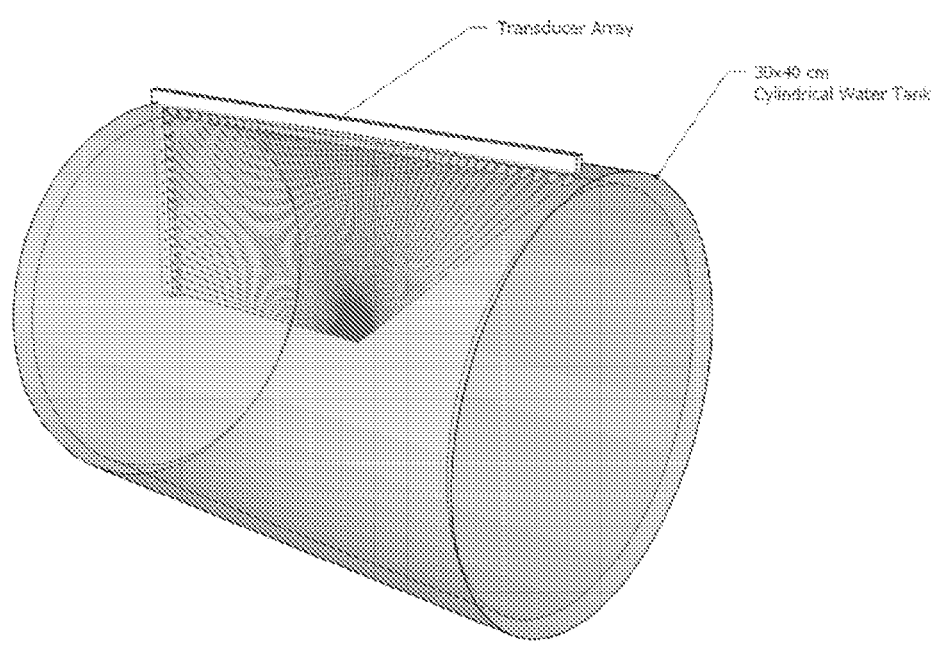
FIG. 7 illustrates the geometry of a transducer array used to simulate the excess pressure created from the dose deposited from a proton beam.
Figure 8:
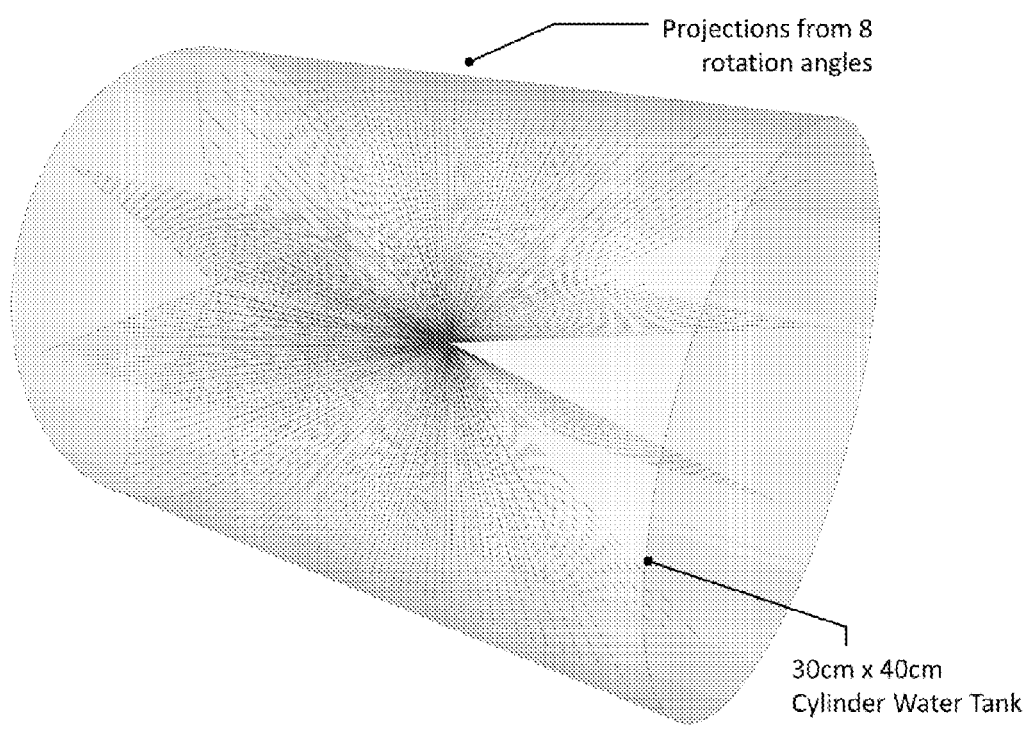
FIG. 8 depicts the rotation of the transducer of FIG. 7 so as to produce a full set of projection angles used to form a volumetric image.

The geometry of the transducer array and a set of projections of the iRCT scanner are displayed in FIG. 7. The transducer array consists of 71 transducers along the surface of a cylinder, with a length of 40 cm and a radius of 15 cm. Each transducer is positioned along the length of the cylinder (z-axis) and the end cap (x-axis), which is opposite to the entrance of the proton beam, and its central axis intersecting the isocenter of the scanner defined 20 cm from the front surface along this central axis. The azimuthal sampling was set to 2.5 degrees. To obtain a full set of projection angles, the scanner was rotated over $2\pi$ every 2.5 degrees (see FIG. 8). A subset of rotation angles and projections are shown in FIG. 8, which resulted in $3\pi$ angular coverage.

Simulation of the Deposited Dose from a Pulsed Pencil Proton Beam

To simulate the dose deposited from a proton beam, a general purpose Monte Carlo code FLUKA (v.2012) was used, where the geometry of a treatment nozzle extracted from the design blueprints were implemented in FLUKA geometry package. The customization set of parameters PRECISIO was used to configure the physical model used in the simulation. The initial proton transport was simulated with a cutoff energy at 100 keV. EMF-CUT card was used to set secondary electron, positron and photon transport. Delta ray production was activated above 100 keV. The energy loss per unit distance (−dE/dx) fluctuations were activated for both water and air below thresholds. The energy cutoffs for secondary electron, positron and photon transport were set to 10 keV. Initial parameters of the proton beam, including the lateral particle fluence and energy spectra, at the nozzle entrance were estimated with the Graphic Turtle Framework code for beam optics. The parameters were tuned based on the comparison between simulation and commissioning measurements, which agree to 2%. For purpose of radiation acoustics study, a three dimensional dose distribution in the cylindrical water phantom from a 200 MeV (27 cm range) and 1.0 cm (FWHM) scanning proton beam was simulated with 0.5 mm voxel size. The dose for each voxel was given in dose per proton.

Radiation-Induced Pressure Signal

Figure 9:
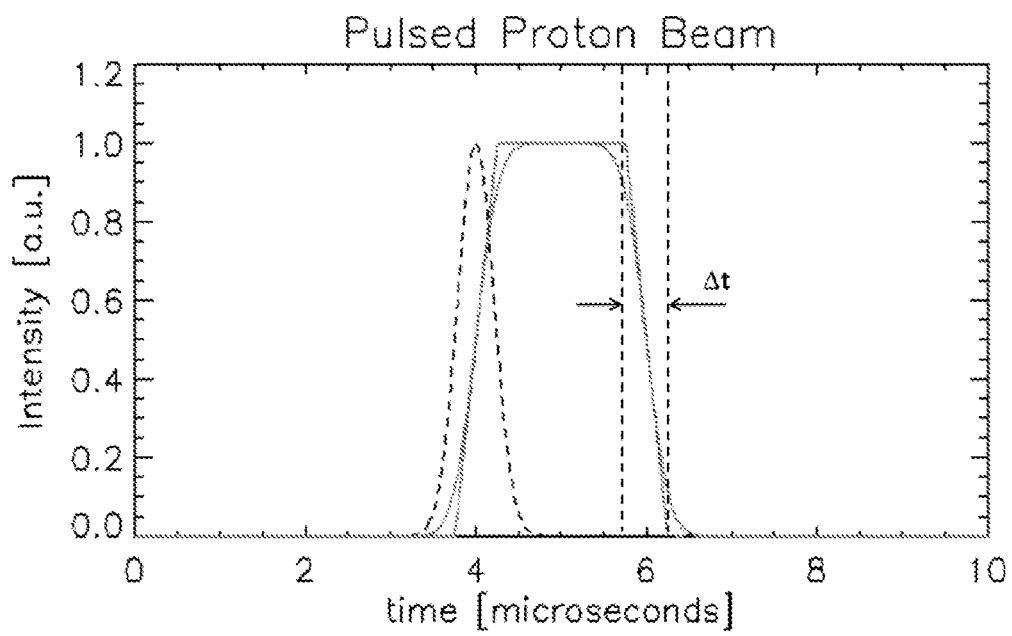
FIG. 9 illustrates a simulated pulsed proton beam defined by $\Im(t)$, where the leading and falling edge is approximated by a linear function which is the derivative at the center of the integrated Gaussian.

To simulate the excess pressure, equation (4) was integrated for each transducer at each rotation angle, using a $\Gamma$ of $1.0 \times 10^5$ [Pa/(J/cm$^3$)], $v_s$ of 1.5 mm/µs, and pulse width as described in FIG. 9. The temporal properties of the pulsed proton beam was modelled as a piece-wise linear function, and the external source term was represented by $$\frac{\partial q_{ext}(r,t)}{\partial t} = \frac{\hat{D}_{i,j,k} \cdot n_P}{(t_{PW} + \Delta t)\Delta t}, \quad (11)$$

where $\hat{D}_{i,j,k}$ is the MC generated dose at each voxel in the water phantom, $n_P$ is the number of protons within a pulse ($1.8 \times 10^7$), $t_{PW}$ is the proton pulse width (at FWHM), and $\Delta t$ the rise-time (in FIG. 9 a 2 µs $t_{PW}$ and 0.2 µs $\Delta t$ is displayed). An acquisition rate of 20 MHz was used to digitally represent the pressure signal.

Reconstruction Algorithm

A 3-D filtered backprojection algorithm is used to reconstruct an image of the dose distributed within the water phantom. For each transducer at each rotation angle, equation (10) was used to calculate the projection, $\hat{\lambda}_{\hat{n}}$. The impulse response of the transducers was simplified using a flat frequency distribution with a wide bandwidth, which was realized using an apodizing function (e.g., Butterworth filter) with a 1 MHz cutoff frequency. This was combined with the ramp function to form the filter function $H(\omega)$. The factor, g, corrected for the geometric weights associated with each projection. This depended on the nonuniformity of sampling over a spherical field-of-view of the scanner, and was defined by the sampling density over a normalized sphere at the isocenter. This predominantly affected the transducers on the end-cap, where the sampling density varied considerably from the transducers along the length of the cylinder. The propagation time, t, was a result of the expanding thermodynamic acoustic wave based on the distance between the source and each transducer. Finally, 2D spherical surfaces of $\hat{\lambda}_{\hat{n}}$ was backprojected to form the dosimetric image. Each reconstructed voxel in the image (0.2 mm) was the sum of the projection from each transducer at each angle and then normalized to total number of projections.

Variation in the Proton Beam Pulse Width and Shape

A feature of the proton beam was the pulse sequence that formed an acoustic signal. The two parameters of interest were the pulse width (PW) and the rise time (RT). The time between pulses should allow enough time for the pressure signal to propagate from the object to each transducer, which should be at least 385 µs (or less than 2.5 KHz). Since signal intensity and sensitivity depends on $t_{PW}$ and $\Delta t$, $t_{PW}$ was simulated at 100, 50, 30, 20, and 10 microseconds, at a Δt of 3 ms, and Δt ranging from 2 to 0.1 μs for the above $t_{PW}$.

3D Dosimetric Image of the Bragg Peak from a Pulsed Proton Beam

Figure 10:
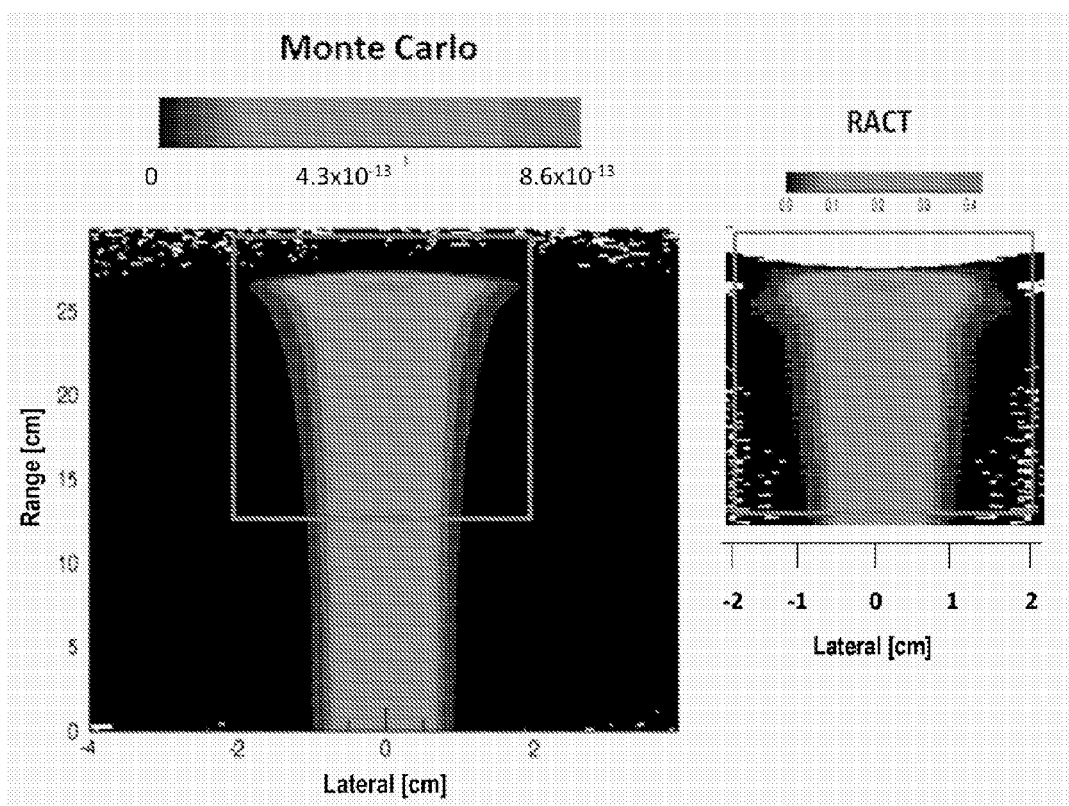
FIG. 10 displays the MC simulated dose (per proton) on a voxel-wise basis for a pencil proton beam with a range of 27 cm (left panel) and the reconstructed image from the radiation acoustic computed tomographic filtered backprojection algorithm (right panel), based on simulated thermaacoustic pressure signal based on localized deposited dose.

The 3D filtered backprojection algorithm was used to reconstruct the dosimetric volume consisting of the Bragg peak, and compared to the MC results. A representative slice along the x-z plane of the MC simulated proton beam and the reconstructed radiation acoustic image is displayed in FIG. 10. A line plot along the central axis demonstrated that the iRCT signal was within 2 percent, on average, of the MC generated dose within the Bragg peak and distal edge, and linearity to dose.

Determining the Proton Range

Figure 11:
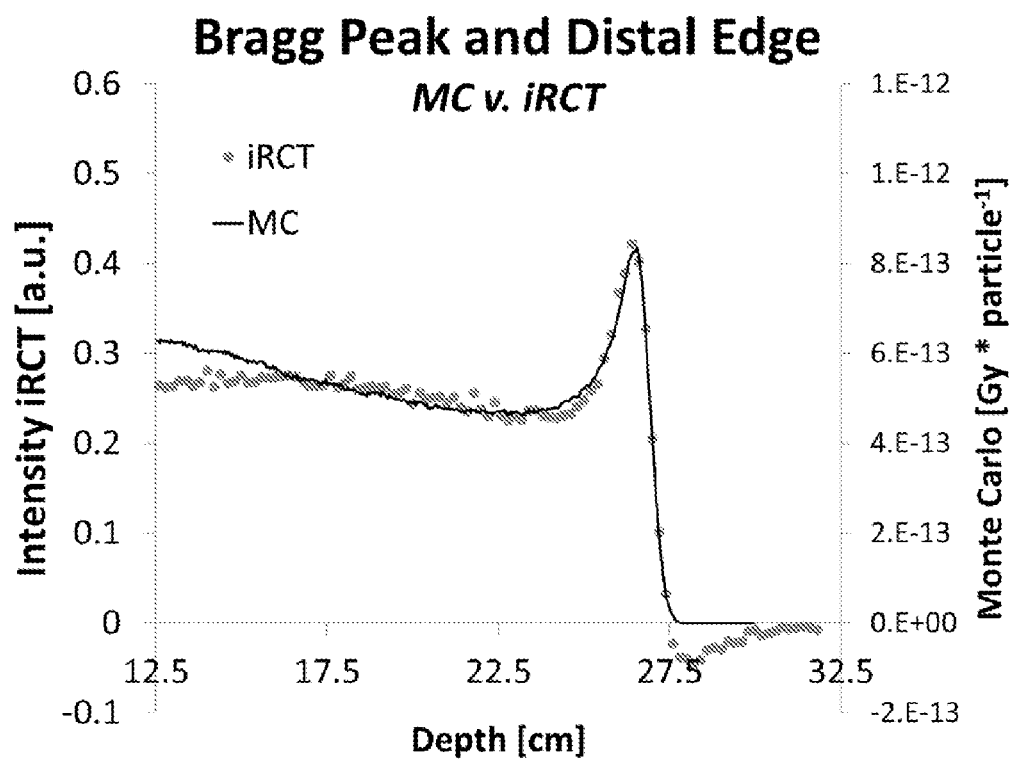
FIG. 11 shows a comparison of the MC dose to the iRCT reconstructed image along the central axis of the scanner.

The position of the distal edge was determined by measuring the 50 percent fall-off point relative to the Bragg peak associated with the distal edge. The position of Bragg peak could be scaled to 90% and 80% of the peak value according to therapeutic proton range definition. By modeling the distal edge as an integrated Gaussian function; the derivative of the curves in FIG. 11 was fit to a Gaussian function, where the values on the rising edge of (proximal to) the Bragg peak was set to zero. Based on these calculations, the location range between iRCT and MC simulated data was within 0.5 mm.

Temporal Properties of the Proton Beam Pulse

Figure 13:
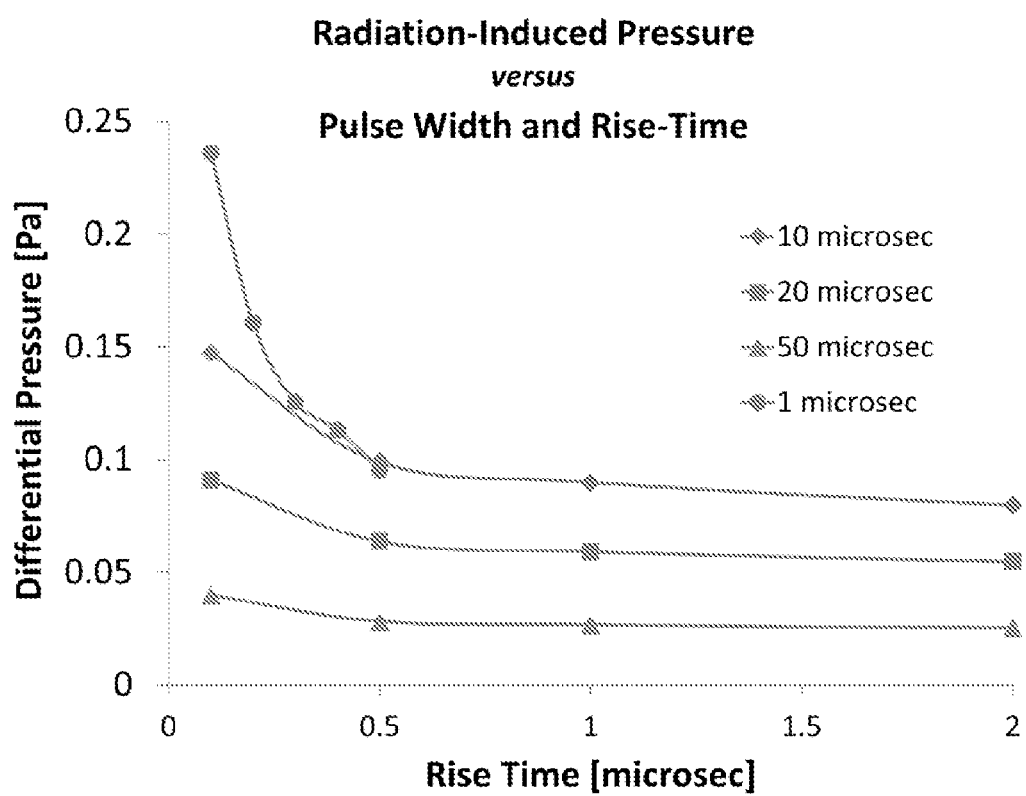
FIG. 13 illustrates the sensitivity of the radioacoustic CT scanner with regards to the pulse width and rise time of the proton beam.

Based on equation (4), the radiation-induce pressure signal, and thus the sensitivity of radio-acoustic CT scanner, depended on both the pulse width ($t_{PW}$) and rise time (Δt) of the proton beam. In FIG. 13, the simulated pressure signal for different $t_{PW}$ and Δt for the same number of protons ($1.8 \times 10^7$) demonstrated that compressing the protons in a shorter period of time (faster beam spill), significantly enhanced the gain of the thermoacoustic signal and sensitivity to dose.

Figure 12:
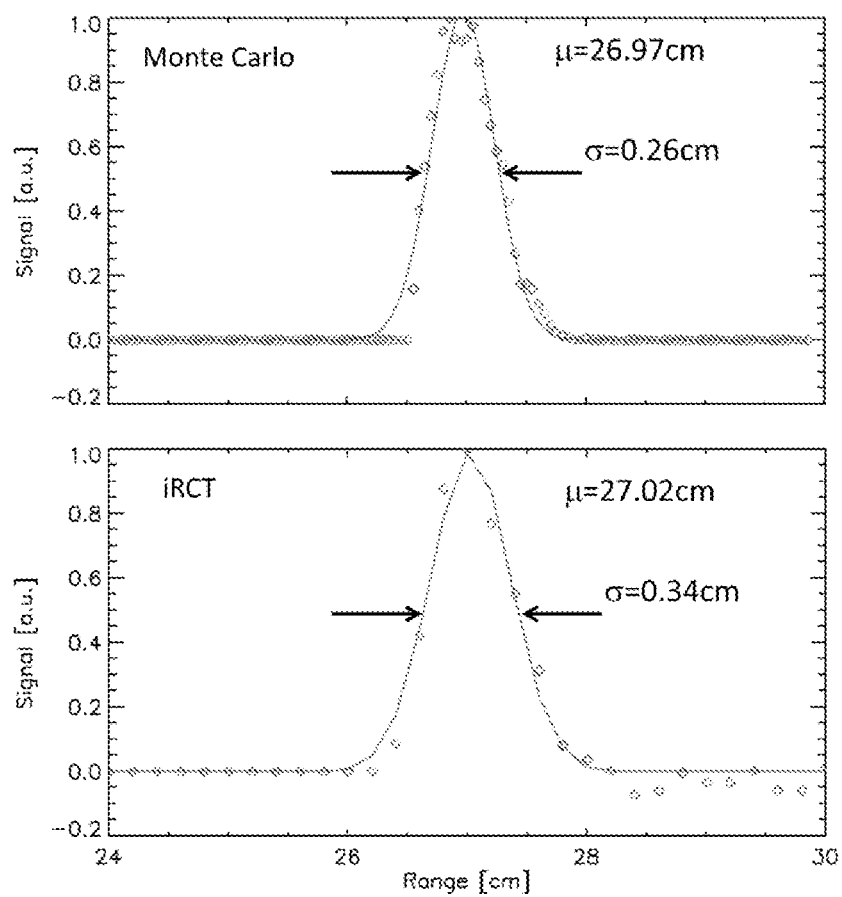
FIG. 12 depicts the modeling of the proton beam as an integrated Gaussian; the derivative of the MC and iRCT curves were fit to a Gaussian function to determine the location of the distal edge, where the iRCT range was 0.3 mm larger that simulated data.

It should be appreciated that current techniques, such as PET and PGs, have been shown to be able to locate the distal edge of proton beams in phantoms with millimeter to a few millimeters accuracy, respectively. However, due to the relatively high activation energy in the formation of PET radioisotopes (11C, 14N, and 15O), the non-linearity of the interaction crossections, and variability of the human tissue elemental composition depends on age, gender, origin and life style. The positron emitter signal does not correspond well to the Bragg peak and location of the distal edge. Through the implementation of computational methods, such as Monte Carlo simulations or convolution of treatment plan with filter functions, the distal fall-off and potentially the dose profile can be obtained. Even though 3-D images are readily obtained, the lack of sensitivity requires in excess of 5 Gy and the relatively long half-life of the radioisotopes makes implementation very challenging. Unlike PET, the PGs activation energy is significantly lower and tracks the deposited dose more closely, to within 2-3 mm of the distal edge. However, PG activity when approaching the proton's range decreases, as does not show sensitivity and linearity. Extensive background from neutrons and stray gammas limit the signal from higher energy PGs used to detect the edge. Disadvantages associated with PET and PGs are addressed with radioacoustic imaging. Initial results based on iRCT dosimetric scanner as presented in 2-D slice plane (FIG. 10) demonstrates the 3-D imaging capabilities of a pulsed proton beam within the scanner described herein. Given that the radioacoustic signal is a direct measurement of dose, a linear relationship between MC dose and iRCT intensities within the field of view (FOV) of the scanner was observed (FIG. 11), the location of the distal edge was determined with sub-millimeter accuracy (FIG. 12), and the dose within the Bragg peak was determined to within 2 percent. Unlike PET or PGs, the proton beam profile and delivery are factors when considering radioacoustic sensitivity, as demonstrated in FIG. 13. These factors include the temporal properties of the pulsed proton beam, as well as the scanner geometry. From equations (4) and (11), the radiation-induced pressure, and thus iRCT intensity, is the integral of the pressure signals from the dose deposited that is weighted by the inverse of proton beam pulse width ($t_{PW}$), rise-time (Δt), and propagation distance. Therefore, when comparing radioacoustic sensitivities, the dose per pulse needs to be normalized relative to $t_{PW}$ and Δt for a given scanner geometry. For example, a 50 nsec pulse width, which would significantly increase radioacoustic pressure (based on FIG. 13). An advantage of the iRCT dosimetric scanner design is that it acquires thousands of projection angles, thus enhancing the signal-to-noise and providing comparable or better sensitivities over a wide range of proton beam pulses.

It should be appreciated that the general purpose Monte Carlo (MC) code FLUK v. 2012 was used for simulation of the proton beam passage through the elements of the treatment nozzle design (FIG. 1). The geometry of the nozzle was extracted from the design blueprints and was implemented in FLUKA geometry package along the beam path through the nozzle as shown in FIG. 1.

The customization set of parameters PRECISIO was used to configure the physical model used in the simulation. The initial proton transport was simulated with a cutoff energy at 100 keV. An EMF-CUT card was used to set secondary electron, positron, and photon transport. Delta ray production was activated above 100 keV. The energy loss per unit distance (−dE/dx) fluctuations were activated for both water and air below thresholds. The energy cutoffs for secondary electron, positron and photon transport were set to 10 keV.

Figure 2A:
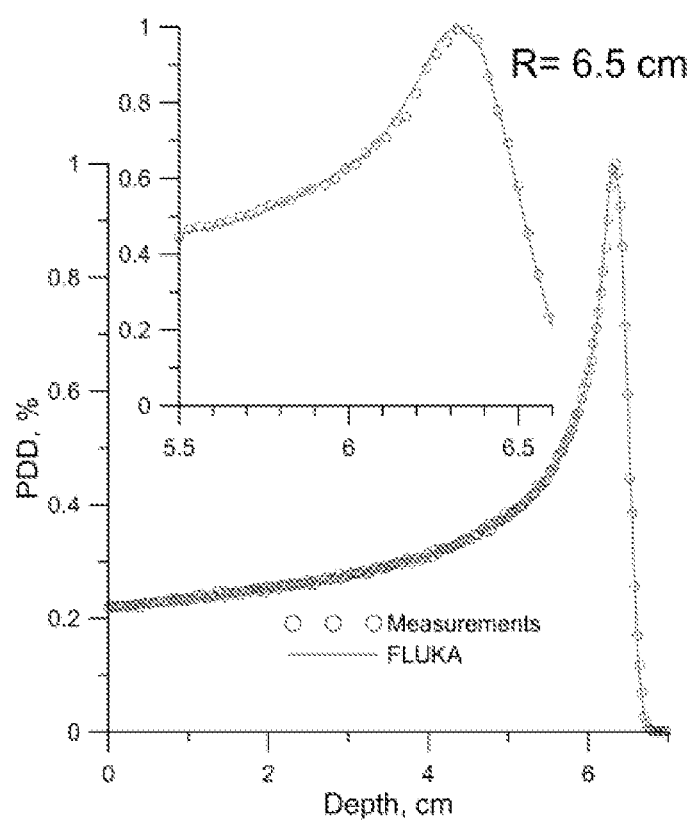
FIG. 2A is a graph that shows the Percentage Depth Dose (PDD) of a proton beam with a range (R) of 6.5 cm in a proton beam uniformly scanned in a case of 10 cm diameter aperture.
Figure 2B:
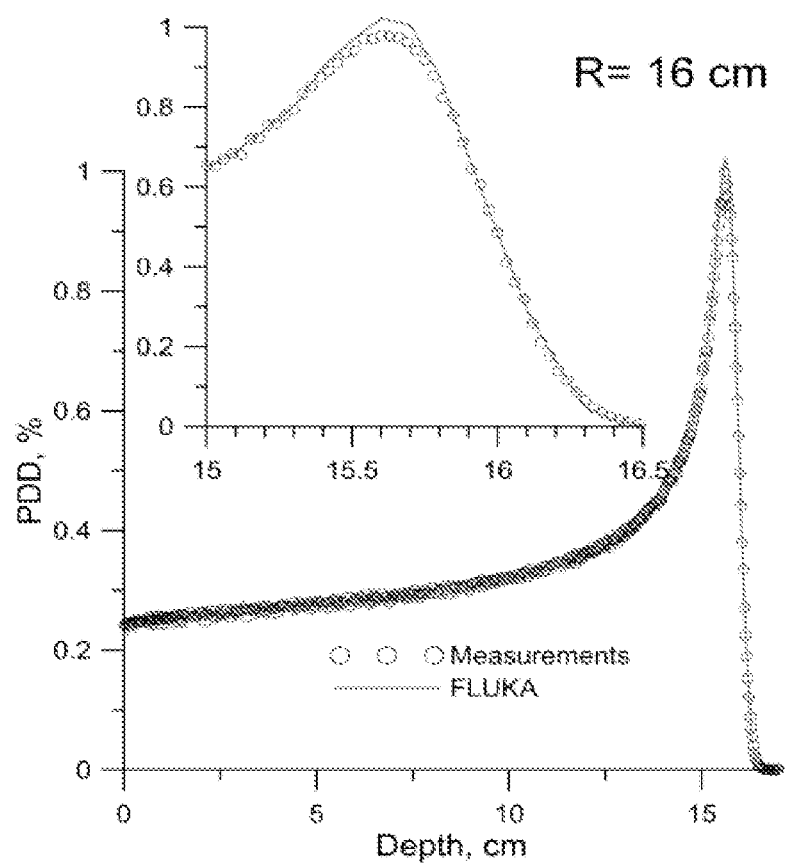
FIG. 2B is a graph that shows the Percentage Depth Dose (PDD) of a proton beam with a range (R) of 16 cm in a proton beam uniformly scanned in a case of 10 cm diameter aperture.
Figure 2C:
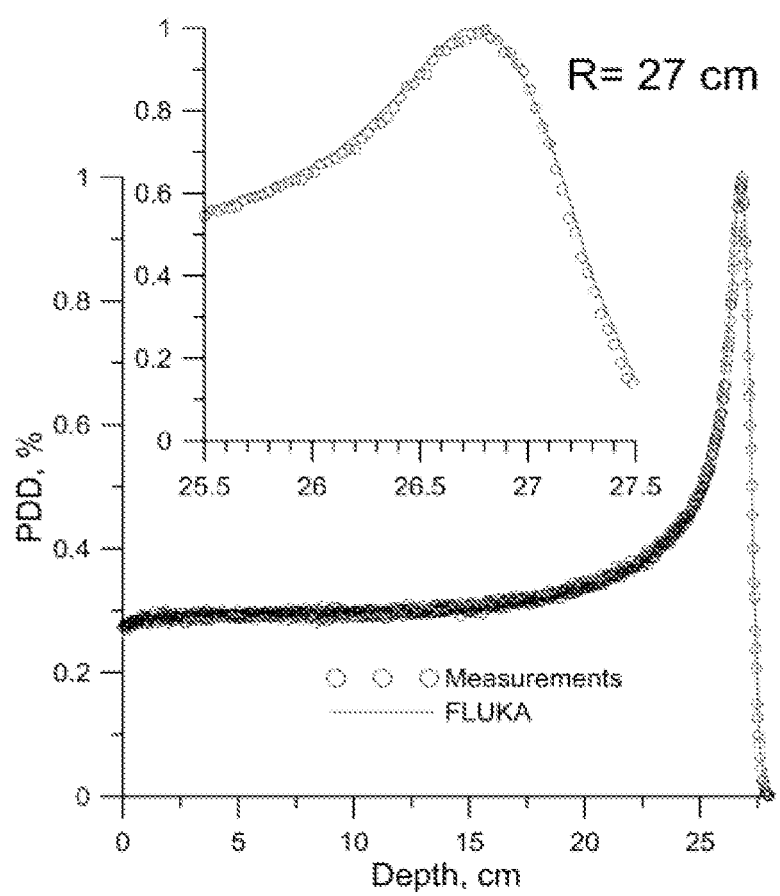
FIG. 2C is a graph that shows the Percentage Depth Dose (PDD) of a proton beam with a range (R) of 27 cm in a proton beam uniformly scanned in a case of 10 cm diameter aperture.

The DOSE command in USRBIN card was used to score dose. Initial parameters of the proton beam (lateral particle fluence and energy spectra), at the nozzle entrance were estimated with the Graphic Turtle Framework code for beam optics. The parameters were tuned based on the comparison between simulation and commissioning range measurements of 6.5 cm, 16 cm, and 27 cm, as shown in FIGS. 2A, 2B, and 2C, respectively. When compared, the parameters agree to about 2%.

Figure 3A:
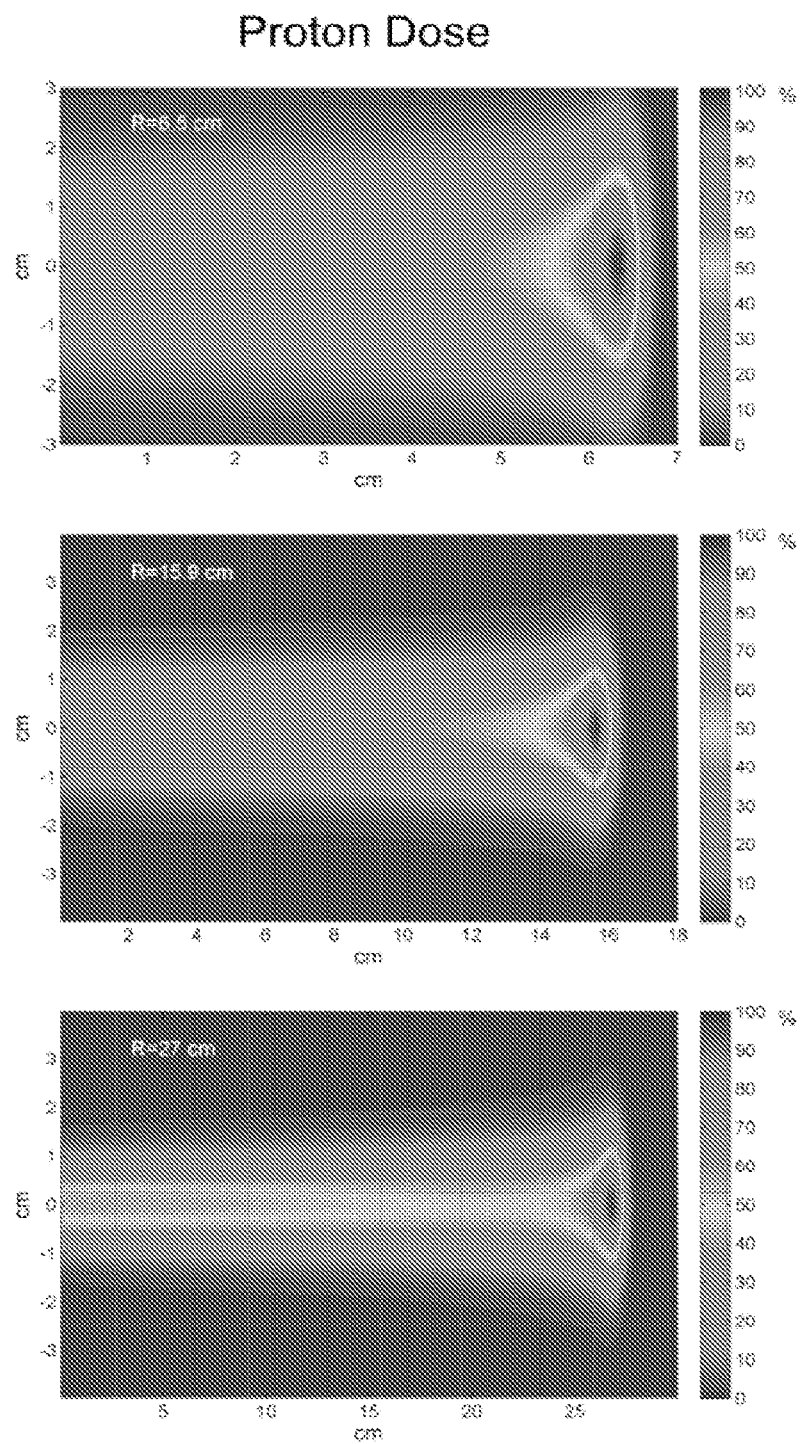
FIGS. 3 A and B show ultrasound signals of the dose and fluence reconstructed from a spot proton beam at a range (R) of 6.5 cm, 15.9 cm, and 27 cm, respectively, in water phantom.
Figure 3B:
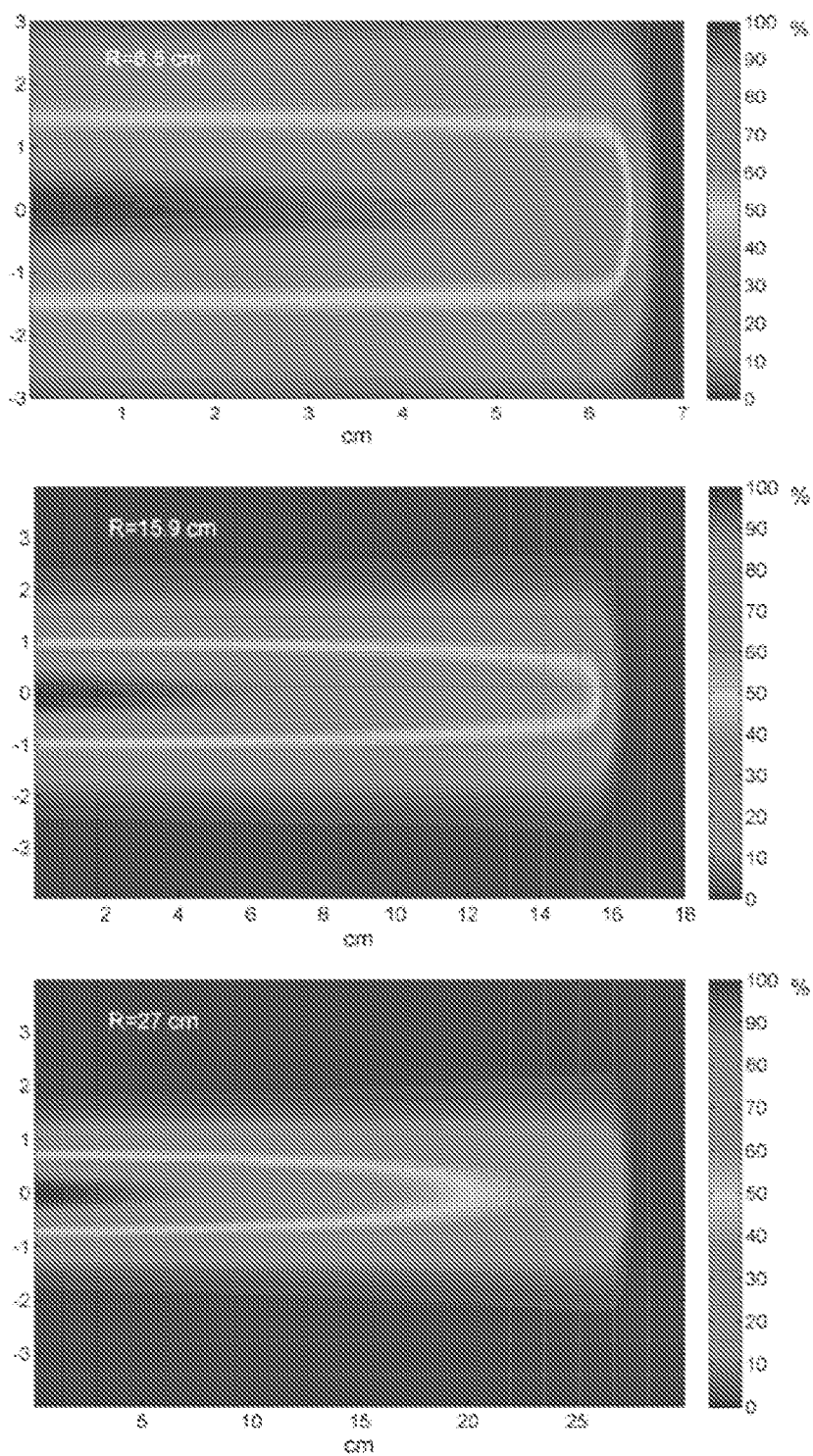

For the purpose of radiation acoustics experiments, the three dimensional dose and proton fluence in water phantom from scanning spot was simulated with 0.05 cm voxel size (FIG. 3B). The phantom was placed at 5 cm air gap from the nozzle. A 3D dose and proton fluence distribution in a water phantom from a scanning spot beam from a treatment nozzle was simulated for 6.5 cm, 15.9 cm, and 27 cm proton ranges, as shown in FIGS. 3A and B.

The reconstruction procedure was implemented within framework of IDL package. The ultrasound signal generated by a spot proton beam was simulated using algorithm of image reconstruction based on thermo-acoustic mechanism. Monte Carlo simulated scanning proton beam dose deposition in water.

Figure 4:
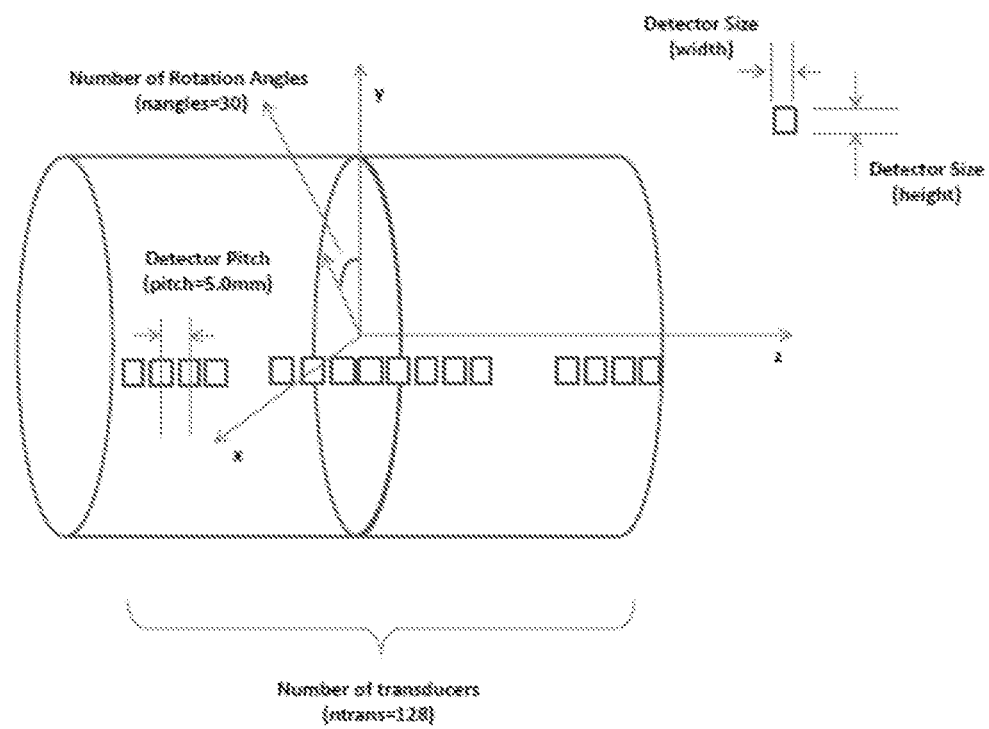
FIG. 4 is a schematic of a Radio-Acoustics Computed Tomography (RCT) Scanner.

As shown in FIG. 4, an initial Radio-acoustic tomographic (RCT) scanner design of a cylinder within a 128 element transducer array (TA) (0.5 MHz center frequency; 50% bandwidth at −6 dB; flat surface) centered along the height of the cylinder (z-axis) at a radial distance of 15 cm was used to generate ultrasound induced signals and evaluated. The ultrasound signals were simulated based on voxel-wise dosimetric data obtained from the above MC simulated (FIGS. 3A and B). As shown in FIG. 4, the TA was rotated implementing a cylindrical geometry over 30 angles about isocenter. A 3D filter backprojection (FBP) algorithm was used to reconstruct dose distribution, particularly, the dosimetric image volume consisting of the Bragg peak (initially at 5×5×5 mm³), and then compared to the MC results (FIGS. 5A and B).

Figure 5A:
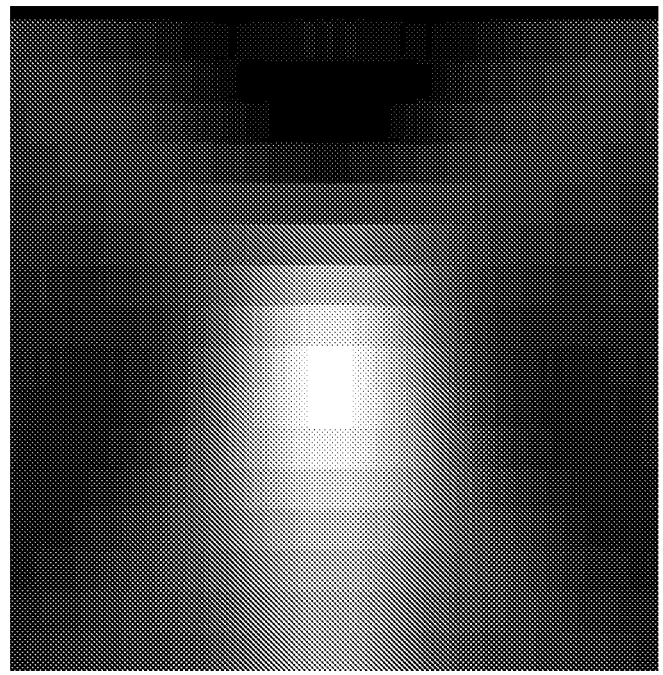
FIG. 5A is a RCT image of the proton Bragg peak.
Figure 5B:
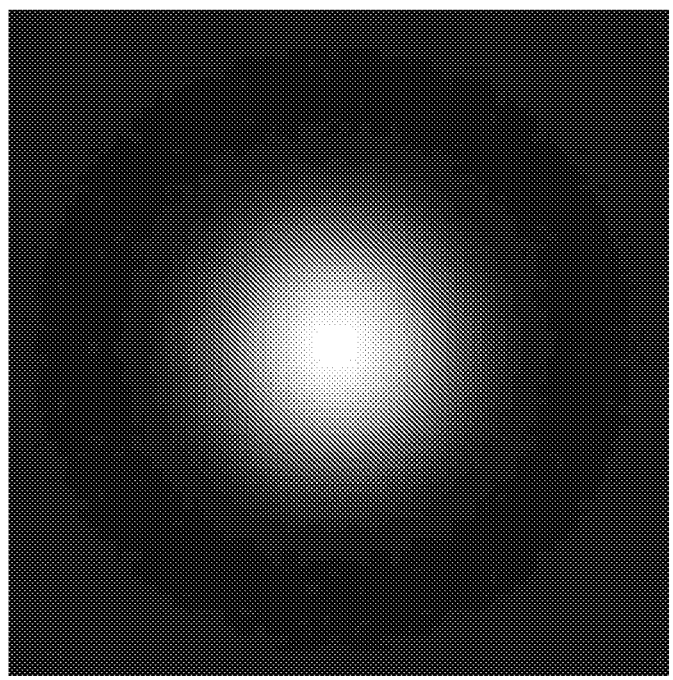
FIG. 5B is a RCT image of the proton beam profile near the Bragg Peak.
Figure 6A:
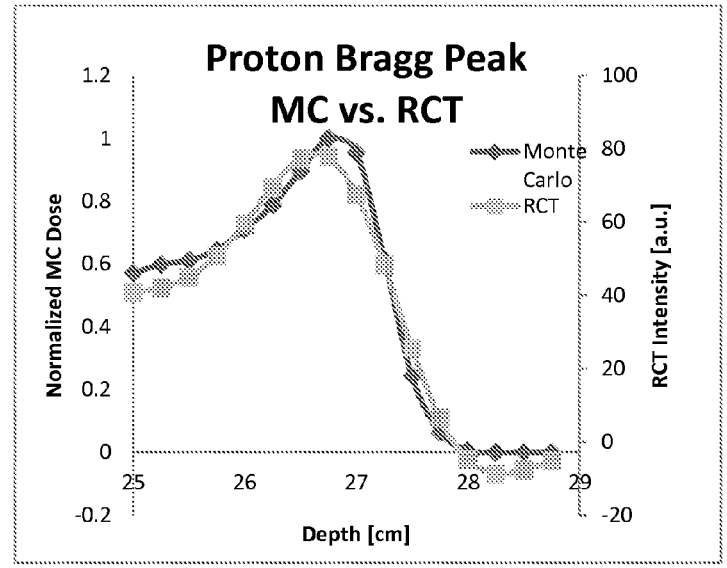
FIG. 6A is a graph comparing RCT-reconstructed data versus MC-reconstructed data at the Bragg Peak.
Figure 6B:
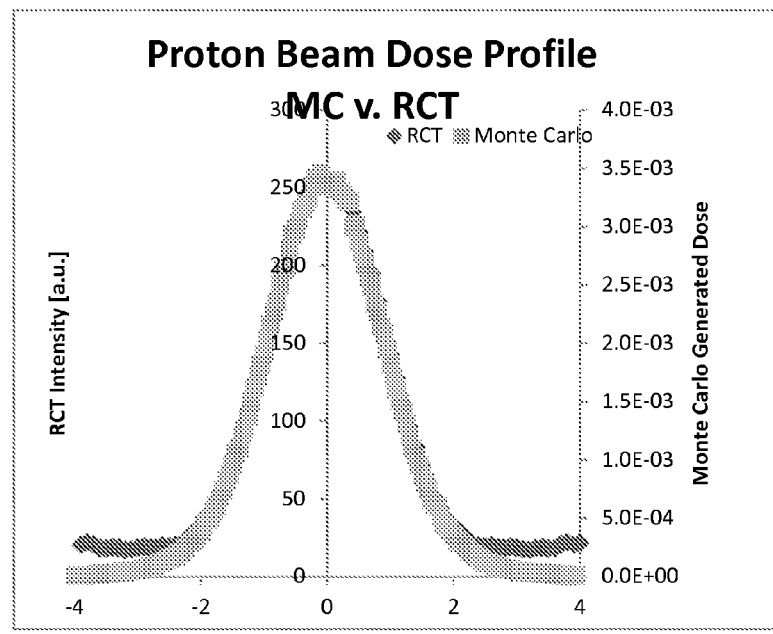
FIG. 6B is a graph comparing the proton beam profile as measured with RCT versus MC.

The RCT dosimetric images are displayed in FIGS. 5 A and B and FIGS. 6 A and B. The proton Bragg peak and proton distal edge are shown in FIGS. 5A and B, respectively. The distal edge of the proton Bragg peak and the beam profile of the MC vs. the RCT signal are shown in FIGS. 6A and 6B, respectively. The units of the MC dose are normalized to the maximum value and the RCT signal exhibits an arbitrary unit. Negative values at the distal edge of the Bragg peak could be a result of artifacts in the RCT reconstruction.

The comparison between the beam profiles as simulated by MC and measured from commissioning of the beam had an estimated deviation of about 2%. An analysis of the RCT intensity dependence on depth as compared to MC simulated data demonstrated that the distal edge of the Bragg peak was within binning size of the reconstruction image and MC position prediction, with an average variation in RCT intensity around 6%. These results demonstrate that RCT can be used to monitor the dose distribution and proton range in proton therapy.

It should be understood that the method of the present disclosure is non-invasive and does not require additional irradiation of patient. The present method is applied at the time of the beam delivery. In addition, the present method disclosure enables the ability to non-invasively image the dose distribution in a patient, the determination of the accuracy and precision of the treatment plan can, and any potential modifications or adaptations over the time of the therapy.

It will be appreciated that the devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples.

Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the disclosure and that the method and apparatus within the scope of these claims and their equivalents be covered thereby. In sum, it should be understood that the disclosure is capable of modification and variation and is limited only by the following claims.

What is claimed:

1. A method of verification of the accuracy of delivery of a charged particle beam to a tumor in a human body, the method comprising:
   irradiating the tumor with the charged particle beam;
   receiving an ultrasound signal generated due to the irradiation of the tumor by the charged particle beam;
   mapping a three dimensional source of the ultrasound signal; wherein the ultrasound signal is formed at the source in the human body due to thermo-acoustic mechanism of a stress wave generation from energy loss of charged particles associated with the charged particle beam; and
   determining a value of falloff of the ultrasound signal corresponding to a distal edge of the charged particle beam associated with a Bragg peak.

2. The method of claim 1, further comprising:
   imaging the source based, at least in part, on the ultrasound signal;
   digitally describing the source based, at least in part, on voxel-wise domestic data; and
   reconstructing spatial energy and dose deposited and range in a direction based, at least in part, on a digital description.

3. The method of claim 1, further comprising:
   real-time comparing of dose distribution reconstructed from the ultrasound signal generated by the charged particle beam associated with treatment planning.

4. The method of claim 1, further comprising:
   real-time mapping of a reconstructed area of a dose delivery at a patient specific computerized tomography image used for acquiring with a cone-beam computerized tomography before a treatment fraction.

5. The method of claim 1, further comprising developing a radioacoustic image of the charged particle beam comprises using ionizing radiation-induced acoustic computed tomography.

6. The method of claim 1, further comprising developing a radioacoustic image of the charged particle beam by:
   applying the charged particle beam to the tumor;
   deriving a pressure wave from the tumor;
   filtering the pressure wave, wherein the filtering is performed by a filter and the filter is a three dimensional filter back-projection algorithm; and
   reconstructing the radioacoustic image from the filtered pressure wave.

7. The method of claim 6, wherein applying the charged particle beam to the tumor comprises applying the charged particle beam to a water phantom.

8. The method of claim 6, wherein developing the radioacoustic image of the charged particle beam comprises developing the radioacoustic image of the charged particle beam using ionizing radiation-induced acoustic computed tomography.

9. The method of claim 8, further comprising comparing the developed radioacoustic image to the Bragg peak and assessing linearity based upon the comparison.

10. The method of claim 6, wherein developing the radioacoustic image of the charged particle beam is based, at least in part, on a Monte Carlo simulation.

11. The method of claim 5, wherein performing ionizing radiation-induced acoustic computed tomography using the charged particle beam comprises using a therapeutic pencil proton beam.

12. A method of performing proton treatment therapy, the method comprising:
   developing a radioacoustic image of a proton beam incident on an in vivo target;
   locating a distal edge of the proton beam from the radioacoustic image; and
   performing the proton treatment therapy based upon the located distal edge of the proton beam.

13. The method of claim 12, wherein developing the radioacoustic image of the proton beam comprises using a Monte Carlo simulation to develop the radioacoustic image.

14. The method of claim 13, wherein developing the radioacoustic image of the proton beam comprises using ionizing radiation-induced acoustic computed tomography.

15. The method of claim 12, wherein the in vivo target is a tumor.

16. The method of claim 12, further comprising:
   applying the proton beam to a sample;
   calculating a pressure wave based, at least in part, on the samples; and
   reconstructing the image from the calculated pressure wave.

17. The method of claim 16, wherein applying the proton beam to the sample comprises applying the proton beam to a water phantom.

18. The method of 12, further comprising comparing the developed radioacoustic image to a Bragg peak and assessing linearity based upon the comparison.

19. The method of claim 2, wherein the voxel-wise dosimetric data is obtained from a Monte Carlo simulation.

20. The method of claim 1, further comprising:
   detecting the ultrasound signal generated by the charged particle beam in the human body with Radio-Acoustic Computed Tomography.

* * * * *

UNITED STATES PATENT AND TRADEMARK OFFICE
CERTIFICATE OF CORRECTION

PATENT NO. : 9,545,527 B2
APPLICATION NO. : 14/888363
DATED : January 17, 2017
INVENTOR(S) : Vadim Moskvin et al.

It is certified that error appears in the above-identified patent and that said Letters Patent is hereby corrected as shown below:

On the Title Page

In the Abstract, please replace:
"A method of verifying therapeutic beam delivery accuracy by ultrasound tomographic imaging to map three dimensional (3D) dose through the detection of ionizing radiation induced thermo-acoustic signal from the proton beam."
To correctly read:
-- A method of verifying therapeutic proton beam delivery accuracy by ultrasound tomographic imaging to map three dimensional (3D) proton dose through the detection of ionizing radiation induced thermo-acoustic signal from the proton beam. --

In the Claims

Column 10, Claim 2, Lines 32 and 33; please replace "reconstructing spatial energy and dose deposited and ranged in a direction base," with -- reconstructing spatial energy and dose deposited and proton range in a direction based, --

Signed and Sealed this
Twenty-seventh Day of March, 2018

Andrei Iancu
*Director of the United States Patent and Trademark Office*